US006353079B1

(12) United States Patent
Walker et al.

(10) Patent No.: US 6,353,079 B1
(45) Date of Patent: Mar. 5, 2002

(54) EPOXY RESIN AND EPOXY DI (METH) ACRYLATE FROM HYDROXYALIPHATIC BISPHENOL

(75) Inventors: Louis L. Walker, Clute; Robert E. Hefner, Jr.; Katherine S. Clement, both of Lake Jackson, all of TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/625,933

(22) Filed: Jul. 26, 2000

Related U.S. Application Data

(60) Provisional application No. 60/146,974, filed on Aug. 3, 1999.

(51) Int. Cl.$^7$ .................... C08G 59/06; C08G 59/17; C07D 303/14; C07D 303/16; C07D 303/18
(52) U.S. Cl. .................... 528/87; 525/524; 525/526; 525/527; 525/528; 525/529; 525/533; 525/531; 528/99; 528/102; 528/112; 549/522; 549/555
(58) Field of Search ................. 549/522, 555; 528/87, 99, 102, 112; 525/524, 526, 527, 528, 529, 531, 533

(56) References Cited

U.S. PATENT DOCUMENTS

| 3,066,112 A | 11/1962 | Bowen |
| 3,179,623 A | 4/1965 | Bowen |
| 3,256,226 A | 6/1966 | Fekete et al. |
| 3,301,743 A | 1/1967 | Fekete et al. ............ 161/194 |
| 3,367,992 A | 2/1968 | Bearden |
| 3,892,819 A | 7/1975 | Najvar ................. 204/159.15 |
| 4,085,160 A | 4/1978 | Anderson et al. ........... 526/204 |
| 4,835,225 A | 5/1989 | Massingill et al. ......... 525/481 |
| 5,115,075 A * | 5/1992 | Brennan et al. ............... 528/99 |
| 5,164,464 A | 11/1992 | Hefner, Jr. et al. ......... 525/531 |
| 5,414,150 A | 5/1995 | Hefner, Jr. et al. ......... 568/729 |
| 5,475,155 A | 12/1995 | Hefner, Jr. et al. ......... 568/727 |
| 5,686,551 A | 11/1997 | White et al. ................ 528/101 |
| 5,723,692 A | 3/1998 | Clement et al. ............ 568/729 |
| 5,723,693 A | 3/1998 | Hefner, Jr. et al. ......... 568/729 |
| 5,736,620 A | 4/1998 | Earls et al. ................. 525/524 |

FOREIGN PATENT DOCUMENTS

| DE | 2619380 | 11/1976 |
| EP | 324405 | 7/1989 |

OTHER PUBLICATIONS

L. R. Whittington, *Whittington's Dictionary of Plastics*, p. 239, 1968.
"Studies in the Photodimerization of the Diglycidyl Ether of 4,4'–Dihydroxychalcone", Journal of Polymer Science, vol. 23, pp. 1355–1372, John Wiley & Sons, Inc., 1979.
G. G. Odian, Principles of Polymerization, John Wiley & Sons, pp. 179–507, 1981.
Spivack, Leib and Lobos, "Novel Pathway for Bacterial Metabolism of Bisphenol A, The Journal of Biological Chemistry", vol. 269, No. 10, pp. 7323–7329, 1994.

* cited by examiner

Primary Examiner—Robert E. L. Sellers

(57) ABSTRACT

The present invention concerns hydroxyaliphatic functional diglycidyl ethers of bisphenols (epoxy resins); curable (thermosettable) mixtures of at least one hydroxyaliphatic functional epoxy resin and at least one curing agent and/or catalyst therefor, as well as cured (thermoset) compositions prepared therefrom; and derivatives prepared therefrom. The bisphenol precursor to the diglycidyl ether contains a hydroxyaliphatic group linkage between the two aromatic rings of the bisphenol.

8 Claims, No Drawings

EPOXY RESIN AND EPOXY DI (METH) ACRYLATE FROM HYDROXYALIPHATIC BISPHENOL

This application claims the benefit of U.S. Provisional Application No. 60/146,974, filed Aug. 3, 1999.

FIELD OF THE INVENTION

The present invention concerns hydroxyaliphatic functional diglycidyl ethers of bisphenols (epoxy resins); curable (thermosettable) mixtures of at least one hydroxyaliphatic functional epoxy resin and at least one curing agent and/or catalyst therefor, as well as cured (thermoset) compositions prepared therefrom; and derivatives prepared therefrom. The bisphenol precursor to the diglycidyl ether contains a hydroxyaliphatic group linkage between the two aromatic rings of the bisphenol.

BACKGROUND AND SUMMARY OF THE INVENTION

The present invention provides novel hydroxyaliphatic epoxy resins, curable mixtures of at least one hydroxyaliphatic functional epoxy resin and at least one curing agent and/or catalyst therefor, as well as the cured (thermoset) compositions prepared therefrom. Epoxy resins are well established as a class of curable compositions which find efficacy in a myriad of applications. The curing of epoxy resins is effected by a wide range of curing agents including, for example, the primary and secondary aliphatic, cycloaliphatic and aromatic polyamines; dicarboxylic acids and the anhydrides thereof; aromatic hydroxyl containing compounds; imidazoles; guanidines; urea-aldehyde resins and alkoxylated derivatives thereof; melamine-aldehyde resins and alkoxylated derivatives thereof; amidoamines; epoxy resin adducts; and various combinations thereof. In addition to said curing agents, one or more catalysts, such as a quaternary ammonium or phosphonium salts are frequently added to accelerate the cure rate as well as to insure completeness of the cure. While the curing of epoxy resins may be effected via the usual epoxy resin curing agents and catalysts, a number of additional factors are critical to and interrelate to the curing process for epoxy resins. These factors include the processing time and temperature profile employed, the epoxide equivalent weight (EEW) of the epoxy resin component(s) employed, the active hydrogen equivalent weight of the curing agent component(s) employed, the final configuration of the curable mixture, and other such variables and combinations of variables. For many of the applications served by epoxy resins, it would be desirable to possess controlled higher reactivity during the curing process, while maintaining, or even improving one or more of the physical and/or mechanical and/or thermal properties of the cured products thereof. The hydroxyaliphatic epoxy resins of the present invention impart controlled higher reactivity during the curing process, while using a wide variety of conventional curing agents and/or catalysts.

The hydroxyaliphatic epoxy resins of the present invention possess a unique molecular structure heretofore unavailable in an epoxy resin. The key feature of the molecular structure inherent to the hydroxyaliphatic epoxy resins of the present invention is the presence of the hydroxy group attached to the aliphatic linkage between the two aromatic rings each bearing a glycidyloxy group. The hydroxy group inherent to the hydroxyaliphatic epoxy resins of the present invention provides curable epoxy resin compositions, with outstanding processability through acceleration of the cure and cured epoxy resin compositions thereof, with substantial improvements in one or more physical and/or mechanical and/or thermal properties. A specific mechanical property expected to be improved by the presence of the aliphatic hydroxy group is adhesion. Furthermore, this improvement is expected, without significantly diminishing the glass transition temperature of the cured epoxy resin. One conventional method for incorporation of aliphatic hydroxy groups into an epoxy resin specifically used to promote adhesion involves partial hydrolysis of epoxide groups to α-glycol groups. However, this markedly lowers the glass transition temperature of the cured epoxy resin by removal of available epoxide groups for reaction with curing agent (lowers the crosslink density). The second conventional method for the incorporation of aliphatic hydroxy groups into an epoxy resin involves advancement of the epoxy resin to produce secondary aliphatic hydroxy groups. This again markedly lowers the glass transition temperature of the cured epoxy resin by forming highly flexible linkages (for example, diether linkages if a diphenol is used in the advancement reaction) between aromatic ring pairs.

Additionally, the hydroxy group inherent to the hydroxyaliphatic epoxy resins of the present invention is present in an exact and defined stoichiometry and thus serves as a convenient reactive site for conversion to a myriad of other functional moieties, thus providing additional epoxy resin compositions of the present invention. Thus, for example, esterification of the hydroxy group with an ethylenically unsaturated carboxylic acid halide, provides a novel thermosettable composition containing both diglycidyl ether and polymerizable ethylenic unsaturation. The resulting diglycidyl ether containing a polymerizable ethylenic unsaturation may be further reacted with an ethylenically unsaturated monocarboxylic acid, such as methacrylic acid, to provide vinyl ester resins containing three or four polymerizable ethylenically unsaturated groups. These novel vinyl ester resins may be thermoset to provide highly crosslinked products. The diglycidyl ether compositions of the present invention containing polymerizable ethylenic unsaturation may be further converted to a polymer modified epoxy resin, via copolymerization with one or more ethylenically unsaturated monomers. Reaction of a polymer modified epoxy resin with an ethylenically unsaturated monocarboxylic acid provides the polymer modified vinyl ester resins of the present invention.

As a further embodiment of the present invention, coupling of a pair of the hydroxyaliphatic epoxy resin molecules, for example via esterification with a diacid halide or, via reaction with a diisocyanate, provides novel tetraglycidyl ethers which can be thermoset to highly crosslinked products. These tetraglycidyl esters may be further reacted with ethylenically unsaturated monocarboxylic acid, such as acrylic acid or methacrylic acid, to provide vinyl ester resins containing four polymerizable ethylenically unsaturated groups. Such polyfunctional vinyl esters are thermosettable to provide highly crosslinked products.

One aspect of the present invention pertains to ydroxyaliphatic epoxy resins or vinyl ester resins represented by the following Formula I

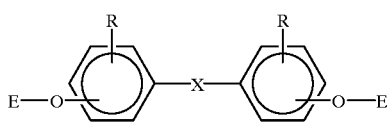

Formula I wherein each R is independently hydrogen or a hydrocarbyl or hydrocarbyloxy group having from one to about 10, preferably one to about 4, carbon atoms, a halogen atom, preferably chlorine, bromine or fluorine, a nitro group, a nitrile group or a —CO—$R^2$ group; E is a

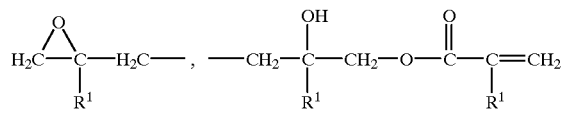

group; each $R^1$ is independently hydrogen or a hydrocarbyl group having from one to about 10, preferably one to about 6, carbon atoms; X is a

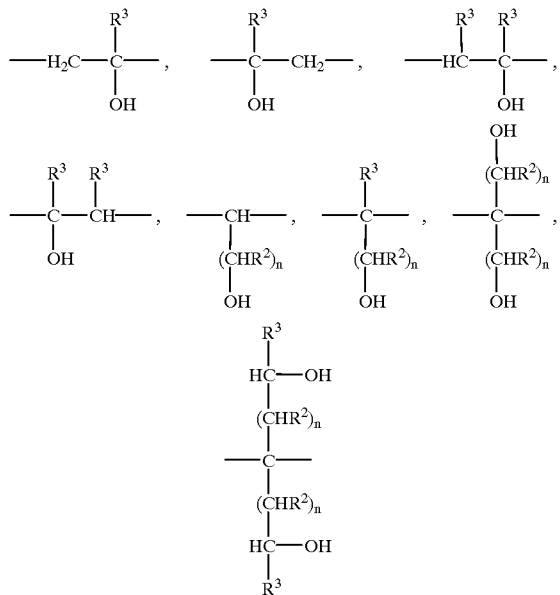

group, each $R^2$ is independently hydrogen or a hydrocarbyl group having from one to about 10, preferably one to about 2, carbon atoms; $R^3$ is a hydrocarbyl group having from one to about 10, preferably one to about 2, carbon atoms; n has a value of from one to about 10, preferably one to about 2.

A further aspect of the present invention pertains to advanced epoxy resins prepared using (A) one or more hydroxyaliphatic epoxy resins, optionally, (B) one or more epoxy resins, and (C) one or more compounds having an average of more than one hydrogen atom per molecule which is reactive with an epoxide group.

Another aspect of the present invention pertains to curable (thermosettable) compositions comprising (A) one or more hydroxyaliphatic epoxy resins, advanced hydroxyaliphatic epoxy resins, or a mixture thereof; optionally, (B) one or more epoxy resins; and (C) a curing amount of one or more curing agents and/or catalysts therefor.

A further aspect of the present invention pertains to products resulting from curing the aforementioned curable compositions.

Another aspect of the present invention pertains to curable (thermosettable) compositions comprising (A) one or more hydroxyaliphatic vinyl ester resins, optionally, (B) one or more vinyl ester resins, optionally, (C) one or more polymerizable ethylenically unsaturated monomers, (D) a curing amount of one or more free radical forming catalysts, and, optionally, (E) one or more curing accelerators.

A further aspect of the present invention pertains to products resulting from curing the aforementioned curable compositions.

A further aspect of the present invention pertains to totally or partially vinylized epoxy and vinyl ester resins represented by the following Formula II (this formula shows total vinylization for the sake of simplicity).

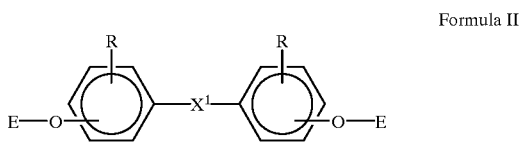

Formula II wherein n, E, R, $R^1$, $R^2$, $R^3$ are as hereinbefore defined, $X^1$ is a

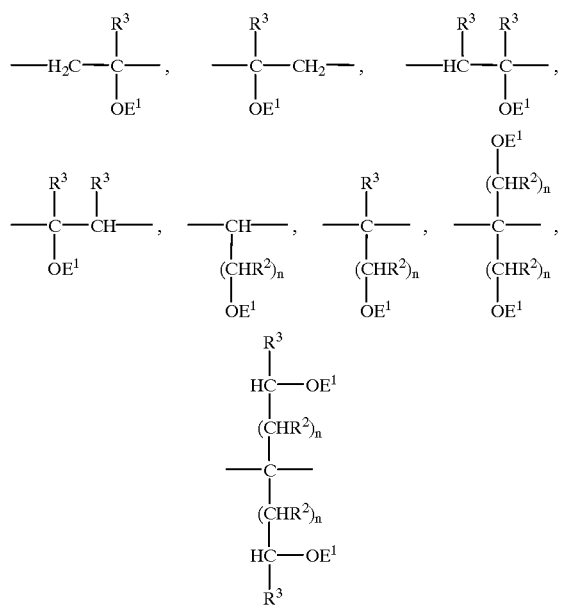

group, $E^1$ is a moiety containing a polymerizable ethylenically unsaturated group wherein the oxygen atom attached to $E^1$ is part of an ester or a urethane linkage.

Another aspect of the present invention pertains to curable (thermosettable) compositions comprising (A) one or more totally or partially vinylized hydroxyaliphatic epoxy resins, optionally, (B) one or more epoxy resins, (C) a curing amount of one or more curing agents and/or catalysts therefor, (D) a curing amount of one or more free radical forming catalysts, and, optionally, (E) one or more curing accelerators.

A further aspect of the present invention pertains to products resulting from curing the aforementioned curable compositions.

Another aspect of the present invention pertains to curable (thermosettable) compositions comprising (A) one or more totally or partially vinylized hydroxyaliphatic vinyl ester resins, optionally, (B) one or more vinyl ester resins, optionally, (C) one or more polymerizable ethylenically unsaturated monomers, (D) a curing amount of one or more free radical forming catalysts, and, optionally, (E) one or more curing accelerators.

A further aspect of the present invention pertains to products resulting from curing the aforementioned curable compositions.

A further aspect of the present invention pertains to tetrafunctional epoxy and vinyl ester resins represented by the following Formulas III and IV

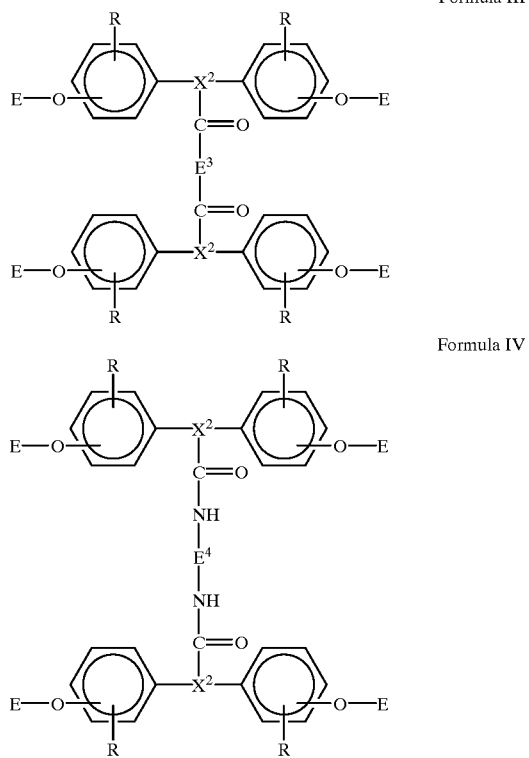

wherein n, E, R, $R^1$, $R^2$, $R^3$ are as hereinbefore defined, $E^3$ is a direct bond or a hydrocarbyl group having from one to about 30, preferably one to about 12, carbon atoms; $E^4$ is a hydrocarbyl group having from about 4 to about 35, preferably six to about 15 carbon atoms; $X^2$ is a

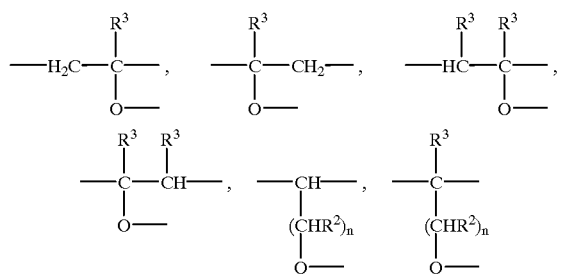

group.

Another aspect of the present invention pertains to curable (thermosettable) compositions comprising (A) one or more tetrafunctional epoxy resins, optionally, (B) one or more epoxy resins; and (C) a curing amount of one or more curing agents and/or catalysts therefor.

A further aspect of the present invention pertains to products resulting from curing the aforementioned curable compositions.

Another aspect of the present invention pertains to curable (thermosettable) compositions comprising (A) one or tetrafunctional vinyl ester, optionally, (B) one or more vinyl ester resins, optionally, (C) one or more polymerizable ethylenically unsaturated monomers, (D) a curing amount of one or more free radical forming catalysts, and, optionally, (E) one or more curing accelerators.

A further aspect of the present invention pertains to products resulting from curing the aforementioned curable compositions.

A further aspect of the present invention pertains to polymer modified epoxy and vinyl ester resins prepared via copolymerization of a partially or totally vinylized monohydroxyaliphatic epoxy resin of Formula II and one or more polymerizable ethylenically unsaturated monomers.

Another aspect of the present invention pertains to curable (thermosettable) compositions comprising (A) one or more polymer modified epoxy resins, optionally, (B) one or more epoxy resins; and (C) a curing amount of one or more curing agents and/or catalysts therefor.

A further aspect of the present invention pertains to products resulting from curing the aforementioned curable compositions.

Another aspect of the present invention pertains to curable (thermosettable) compositions comprising (A) one or more polymer modified vinyl ester resins, optionally, (B) one or more vinyl ester resins, optionally, (C) one or more polymerizable ethylenically unsaturated monomers, (D) a curing amount of one or more free radical forming catalysts, and, optionally, (E) one or more curing accelerators.

A further aspect of the present invention pertains to products resulting from curing the aforementioned curable compositions.

DETAILED DESCRIPTION OF THE INVENTION

Definitions

The term "hydrocarbyl" as employed herein means any aliphatic, cycloaliphatic, aromatic, aryl substituted aliphatic or cycloaliphatic or aliphatic or cycloaliphatic substituted aromatic groups. The aliphatic or cycloaliphatic groups can be saturated or unsaturated. The aliphatic groups can be straight chained or branched. Likewise, the term "hydrocarbyloxy" means a hydrocarbyl group having an oxygen linkage between it and the carbon atom to which it is attached.

The term "hydroxyaliphatic" means an aliphatic group, such as an alkylene or alkenylene, which is substituted with one or more hydroxy groups and is divalent, that is, it has two attachment points as shown for X in Formula I and $X^1$ in Formula II.

The terms "curable" and "thermosettable" are used synonymously throughout and mean that the composition is capable of being subjected to conditions which will render the composition to a cured or thermoset state or condition.

The terms "cured" and "thermoset" are used synonymously throughout. The term "thermoset" is defined by L. R. Whittington in *Whittington's Dictionary of Plastics* (1968) on page 239: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

Hydroxyaliphatic Epoxy Resins and Advanced Epoxy Resins

The hydroxyaliphatic epoxy resins of the present invention can be prepared using known methods. Thus, hydroxyaliphatic epoxy resins are generally prepared by reacting a bis(hydroxyphenyl)hydroxyaliphatic compound with an epihalohydrin in the presence of a suitable catalyst and in the presence or absence of a suitable solvent at a temperature suitably from about 0° C. to about 100° C., more suitably from about 20° C. to about 80° C., most suitably from about 20° C. to about 65° C.; at pressures suitably from about 30 mm Hg vacuum to about 100 psia, more suitably from about 30 Hg vacuum to about 50 psia, most suitably from about 60 mm Hg vacuum to about atmospheric pressure; for a time sufficient to complete the reaction, usually from about 0.5 to about 24, more usually from about 1 to about 12, most usually from about 1 to about 8 hours; and using from about 1.5:1 to 100:1, preferably from about 2:1 to about 50:1, most preferably from about 3:1 to about 20:1 moles of epihalohydrin per phenolic hydroxy group. This initial reaction, unless the catalyst is an alkali metal or alkaline earth metal hydroxide employed in stoichiometric quantities, produces a halohydrin intermediate which is then reacted with a basic acting substance to convert the vicinal halohydrin groups to epoxide groups. The resultant product is a glycidyl ether compound, wherein the aliphatic hydroxy group remains essentially unchanged. Details concerning preparation of epoxy resins are given in U.S. Pat. No. 5,736,620; Handbook of Epoxy Resins by Lee and Neville, McGraw-Hill (1967); and Journal of Applied Polymer Science, volume 23, pages 1355–1372 (1972) all of which are incorporated herein by reference in their entirety.

The hydroxyaliphatic epoxy resin's chain may be linearly extended via an advancement reaction. Such advancement may be desirable to increase molecular weight. The increase in molecular weight is useful to vary the mechanical properties and to control the degree of crosslinking.

Advancement reaction of a hydroxyaliphatic epoxy resin can be performed using known methods which usually includes combining one or more suitable compounds having an average of more than one hydrogen atom per molecule which is reactive with an epoxy group, including, for example, dihydroxy aromatic, dithiol, disulfonamide or dicarboxylic acid compounds or compounds containing one primary amine or amide group, two secondary amine groups, one secondary amine group and one phenolic hydroxy group, one secondary amine group and one carboxylic acid group, or one phenolic hydroxy group and one carboxylic acid group and the hydroxyaliphatic epoxy resin in the presence or absence of a suitable solvent with the application of heat and mixing to effect the advancement reaction. The compound having more than one hydrogen atom per molecule which is reactive with an epoxide group and the hydroxyaliphatic epoxy resin are reacted in amounts which provide suitably from about 0.01:1 to about 0.95:1, more suitably from about 0.05:1 to about 0.8:1, most suitably from about 0.10:1 to about 0.5:1 reactive hydrogen atoms per epoxide group. The advancement reaction can be conducted at atmospheric, superatmospheric or subatmospheric pressures at temperatures of from about 20° C. to about 260°C., more suitably from about 80° C. to about 240° C., most suitably from about 100° C. to about 200° C. The time required to complete the advancement reaction depends upon the temperature employed, the structure of the active hydrogen-containing compound employed, the structure of the hydroxyaliphatic epoxy resin employed and other such variables. Higher temperatures require shorter periods of time whereas lower temperatures require longer periods of time. Generally, times of from about 5 minutes to about 24 hours, more suitably from about 30 minutes to about 8 hours, most suitably from about 30 minutes to about 4 hours are employed. A catalyst, including, for example, phosphines, quaternary ammonium compounds, phosphonium compounds and tertiary amines, is frequently added to facilitate the advancement reaction and is usually employed in quantities of from about 0.01 to about 3, preferably from about 0.03 to about 1.5, most preferably from about 0.05 to about 1.5 percent by weight based upon the weight of the hydroxyaliphatic epoxy resin. Details concerning advancement reaction are given in the aforementioned U.S. Pat. No. 5,736,620 and Handbook of Epoxy Resins.

The curable compositions of the present invention are prepared by mixing together one or more of the hydroxyaliphatic epoxy resins, advanced hydroxyaliphatic epoxy resins, mixtures thereof, or mixtures with epoxy resins and one or more curing agents and/or curing catalysts therefor in amounts which will effectively cure the mixture, with the understanding that these amounts will depend upon the particular epoxy resin and curing agent employed. Generally, suitable amounts of curing agents are from about 0.80:1 to about 1.50:1, preferably from about 0.95:1 to about 1.05:1 equivalents of hydrogen in the curing agent which is reactive with an epoxide group per equivalent of epoxide group in the hydroxyaliphatic epoxy resin at the conditions employed for curing.

The curing of the curable compositions of the present invention can be conducted at atmospheric, superatmospheric or subatmospheric pressures at temperatures of from about 0° C. to about 300° C., preferably from about 50° C. to about 200° C., more preferably from about 80° C. to about 175° C. The time required to complete curing depends upon the temperature employed. Higher temperatures require shorter periods of time whereas lower temperatures require longer periods of time. Generally, however, times of from about one minute to about 48 hours, preferably from about 15 minutes to about 8 hours, more preferably from about 30 minutes to about 3 hours are suitable. It is also operable to partially cure (B-stage) the curable compositions of the present invention and then complete the curing at a later time.

The curable mixtures of the present invention may be prepared using the known conventional curing agents and/or catalysts for curing epoxy resins, such as, for example, aliphatic, cycloaliphatic, polycycloaliphatic or aromatic primary monoamines; aliphatic, cycloaliphatic, polycycloaliphatic or aromatic primary and secondary polyamines; carboxylic acids and anhydrides thereof; aromatic hydroxyl containing compounds; imidazoles; guanidines; urea-aldehyde resins; melamine-aldehyde resins; alkoxylated urea-aldehyde resins; alkoxylated melamine-aldehyde resins; amidoamines; epoxy resin adducts; combinations thereof and the like. Particularly suitable curing agents include, for example, methylenedianiline, 4,4'-diaminostilbene, 4,4'-diamino-α-methylstilbene, 4,4'-diaminobenzanilide, dicyandiamide, ethylenediamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylamine, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

Particularly suitable curing catalysts include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, mixtures thereof and the like.

The curing catalysts are employed in amounts which will effectively cure the curable composition, however, these amounts will depend upon the particular hydroxyaliphatic epoxy resin employed and curing agent, if used. Generally suitable amounts include, for example, 0.001 to about 2 percent by weight of the total hydroxyaliphatic epoxy resin used. It is frequently of benefit to employ one or more of the curing catalysts in the curing of the curable compositions of the present invention. This is generally done to accelerate or otherwise modify the curing behavior obtained when a curing catalyst is not used.

Phenoxy Resins

Phenoxy resins of the present invention are prepared via advancement reaction of at least one hydroxyaliphatic epoxy resin and at least one compound having more than one hydrogen atom per molecule which is reactive with an epoxide group, wherein said difunctional monomer and said diglycidyl ether are reacted in amounts which provide suitably from about 0.96:1 to about 1.05:1, more suitably from about 0.98:1 to about 1.03:1, most suitably about 1:1 reactive hydrogen atoms per epoxide group. The resulting phenoxy resin is a substantially thermoplastic, resinous product which contains little, if any, residual curable epoxide functionality and may even contain an active hydrogen functionality, depending on which component, if any, is employed in excess, the hydroxyaliphatic epoxy resin or the epoxide reactive hydrogen-containing compound. Details concerning advancement reaction to produce phenoxy resins are given in the aforementioned U.S. Pat. No. 5,736,620 and in U.S. Pat. No. 5,686,551 which is incorporated herein by reference in its entirety. Additionally, residual epoxide groups, if present in the phenoxy resin, may be "end-capped" via reaction with monofunctional reactants (compounds having one hydrogen atom which is reactive with an epoxide group) such as carboxylic acids, thiols, monofunctional sulfonamides, secondary amines, and monohydric phenols. Preferred monofunctional reactants include acetic acid, benzoic acid, thiophenol, N-methylbenzensulfonamide, diethanolamine, N-(2-hydroxyethyl)piperazine, N-methylpiperazine, phenol, and tert-butylphenol. Reaction conditions for conducting said end-capping reaction are identical to those previously delineated herein for the advancement reaction. In fact, end-capping reaction with the monofunctional reactant may be performed as an integral part of the advancement reaction, for example, by adding said monofunctional compound at or near the completion of the advancement reaction. It is frequently advantageous to end-cap the phenoxy resin of the present invention to remove residual epoxide groups which may react during processing to form crosslinks which are deleterious to thermoplastic character.

Hydroxyaliphatic Vinyl Ester Resins

The hydroxyaliphatic vinyl ester resins of the present invention can be prepared using known methods. Thus, the hydroxyaliphatic epoxy resins, advanced hydroxyaliphatic epoxy resins, mixtures thereof, or mixtures with epoxy resins are generally reacted with one or more suitable monounsaturated monocarboxylic acids, namely acrylic acid or methacrylic acid. Other less preferred, but operable monounsaturated monocarboxylic acids include cyanoacrylic acid, crotonic acid, α-phenylacrylic acid, methoxyacrylic acid, monomethyl ester of maleic acid, monomethyl ester of fumaric acid, mixtures thereof and the like. Methacrylic acid is the most preferred monounsaturated monocarboxylic acid. A mole ratio of 0.9:1.1 monounsaturated monocarboxylic acid per epoxide group is preferred, with a mole ratio of 0.95: 1.00 being most preferred. The reaction between the carboxylic acid group and the epoxide group is typically performed in the presence of one or more catalysts. Chromium trichloride and tris (dimethylaminoethyl)phenol are most preferred as the catalysts. A quantity of from about 0.01 to about 2 percent by weight has been found to be a suitable quantity of catalyst with concentrations of 0.1 to 0.3 weight percent of the total reactants used being most preferred. A suitable process inhibitor is typically used in the reaction between the epoxide group and the carboxylic acid group to prevent gelation. Hydroquinone activated with air is a most preferred inhibitor at concentrations of from about 100 ppm to about 500 ppm based on the total weight of the reactants used. The reaction to produce the hydroxyaliphatic vinyl ester compositions of the present invention is optionally conducted in one or more organic solvents inert to the other reactants and the vinyl ester product. Typical of the inert organic solvents are the aliphatic ketones, such as methylisobutyl ketone; the chlorinated aliphatics, such as perchloroethylene; and the aromatic hydrocarbons, such as toluene. The reaction to produce the hydroxyaliphatic vinyl ester resin is usually conducted at a temperature of from about 50° C. to about 125° C., preferably from about 80° C. to about 120° C. for from about 90 minutes to 720 minutes, preferably from about 120 minutes to about 420 minutes. While reaction times and temperatures can vary substantially, the most preferred hydroxyaliphatic vinyl esters are produced by reacting to a specific conversion, typically 1.5 to 0.25 percent carboxylic acid.

The vinyl ester is typically combined with a reactive diluent, a copolymerizable ethylenically unsaturated monomer, to alter the viscosity of the mixture, to vary properties of the cured resin, or for other known reasons. Suitable ethylenically unsaturated monomers which can be employed herein can be selected from the many known classes of polymerizable monomers. Suitable such monomers include, for example, the vinyl aromatic compounds, such as styrene, α-methylstyrene, vinyl toluenes, halogenated styrenes, t-butylstyrenes, vinyl naphthalenes, and divinylbenzenes. Other suitable monomers include the methyl, ethyl, isopropyl, octyl, etc. esters of acrylic and methacrylic acid, hydroxyethyl acrylate and methacrylate, hydroxypropyl acrylate and methacrylate; acidic monomers, such as acrylic acid, methacrylic acid and crotonic acid; amide monomers, such as, acrylamide and N-alkylacrylamides; allyl monomers, such as diallylphthalate, triallylisocyanurate, diallylmaleate and dimethallyl fumarate; vinyl acetate; mixtures thereof and the like. The reactive diluent present in the copolymerizable mixtures of the present invention can consist of 1 to 99, preferably from about 20 to about 80, most preferably 30 to about 70 percent by weight of the combined weight of said reactive diluent and vinyl ester. If an inert organic solvent is used in the preparation of the vinyl ester, it is preferably removed, for example by distillation under vacuum, prior to the addition of one or more ethylenically unsaturated monomers.

The vinyl ester and the blend of the vinyl ester with an ethylenically unsaturated monomer are curable, typically by mixing in a free radical forming catalyst and applying heat and/or pressure and/or adding an accelerator. Catalysts that can be used for the curing include the peroxide catalysts, such as benzoyl peroxide, lauroyl peroxide, tert-butylhydroperoxide, methyl ethyl ketone peroxide, tert-butylperoxybenzoate, potassium persulfate, mixtures thereof and the like. The amount of catalyst added will vary from 0.1 to about 2 percent by weight, preferably from about 0.75 to 1.5 percent by weight. Temperatures employed can vary over a considerable range but are usually in the range of 20° C. to 250° C. Additionally, more rapid curing of the vinyl ester compositions can be accomplished by the addition of one or more accelerators, such as lead or cobalt naphthenate, N,N,-dimethylaniline, mixtures thereof and the like, usually in concentrations ranging from about 0.01 to about 2 percent by weight, preferably 0.05 to 0.5 percent by weight. Details concerning preparation of vinyl ester resins are given in U.S. Pat. Nos. 3,367,992; 3,066,112; 3,179,623; 3,301,743; 3,256,226; 3,892,819; 5,164,464 all of which are incorporated herein by reference in their entirety.

Vinylized Epoxy and Vinyl Ester Resins Derived from Hydroxyaliphatic Epoxy Resins Vinylized epoxy and vinyl ester resins are prepared via reaction of one or more hydroxyaliphatic epoxy resins with one or more compounds possessing a group reactive with the hydroxy group(s) in said hydroxyaliphatic epoxy resin and a single polymerizable ethylenically unsaturated group. It is understood, as a specific embodiment of the present invention, that all or only a part of said hydroxy group(s) may be reacted (vinylized) to a polymerizable ethylenic unsaturated group. The resulting product is an epoxy resin containing polymerizable ethylenic unsaturation, wherein all or only a part of the hydroxy group(s) have been converted to groups containing polymerizable ethylenic unsaturation. The vinylized vinyl ester resins of the present invention are prepared using the partially or totally vinylized epoxy resins and methods previously delineated herein for the preparation of vinyl ester resins.

Suitable compounds which are reacted with the hydroxyaliphatic epoxy resin to provide the vinylized epoxy resin include most any compound possessing a group reactive with the hydroxy group in said hydroxyaliphatic epoxy resin and a polymerizable ethylenically unsaturated group. Representative of said compounds are the ethylenically unsaturated carboxylic acid halides, such as, for example, acryloyl chloride, methacryloyl bromide, methacryloyl chloride; the monoesterified α,β-unsaturated dicarboxylic acid halides, such as, for example, fumaric acid chloride methyl monoester, itaconic acid chloride ethyl monoester; and the ethylenically unsaturated monoisocyanates, such as, for example, p-isopropenyl phenylisocyanate, isocyanatoethylmethacrylate. Most preferred as the compound for the vinylization of the hydroxyaliphatic epoxy resin is acryloyl chloride or methacryloyl chloride. These compounds containing a group reactive with the hydroxy group in the hydroxyaliphatic epoxy resin and a polymerizable ethylenically unsaturated group are employed in amounts which result in the desired degree of vinylization. Thus, using less than the stoichiometric amount of the compound containing a group reactive with the hydroxy group in the hydroxyaliphatic epoxy resin and a polymerizable ethylenically group per hydroxy group contained in the hydroxyaliphatic epoxy resin results in partial vinylization. Likewise, stoichiometric (or slight stoichiometric excess) use of these reactants results in total vinylization of the hydroxyaliphatic epoxy resin. The vinylization reaction is usually conducted at temperatures of from about −20° C. to about 80° C., preferably from about 0° C. to about 50° C., more preferably from about 10° C. to about 30° C. A suitable basic acting substance is employed to facilitate reaction of an ethylenically unsaturated carboxylic acid halide or monoesterified α,β-unsaturated dicarboxylic acid halide with the hydroxy group of the hydroxyaliphatic epoxy resin. Said basic acting substance additionally serves to scavenge hydrogen halide generated during the vinylization reaction, thus preventing undesirable reaction with epoxide groups. Suitable basic acting substances include the alkali metal or alkaline earth metal hydroxides, carbonates and bicarbonates, trialkyl monoamines, or mixtures thereof. Particularly suitable such compounds include sodium carbonate, potassium carbonate, sodium bicarbonate, potassium bicarbonate, magnesium carbonate, calcium carbonate, triethylamine, tri-n-butylamine, tri-tert-butylamine, mixtures thereof and the like. Care should be taken to utilize only those basic acting substances which are inert to reaction with any of the reactants employed in the vinylization reaction or the product formed therefrom. The vinylization reaction is advantageously conducted in the presence of one or more solvents. Suitable such solvents include aliphatic and aromatic hydrocarbons, halogenated aliphatic hydrocarbons, aliphatic ethers, cyclic ethers, ketones, esters, amides, sulfoxides, combinations thereof and the like. Particularly suitable solvents include pentane, hexane, octane, toluene, methyl ethyl ketone, methylisobutyl ketone, dimethylformamide, dimethylsulfoxide, diethyl ether, methyl acetate, ethyl acetate, tetrahydrofuran, 1,4-dioxane, methylene chloride, chloroform, ethylene dichloride, methyl chloroform, ethylene glycol dimethyl ether, combinations thereof and the like. The solvent may be removed at the completion of the reaction using conventional means, such as, for example, vacuum distillation. Care should be taken to utilize only those solvents which are inert to reaction with any of the reactants employed in the vinylization reaction or the product formed therefrom.

Tetrafunctional Epoxy and Vinyl Ester Resins Derived from Hydroxyaliphatic Epoxy Resins Tetrafunctional epoxy and vinyl ester resins are prepared via coupling reaction of one or more monohydroxyaliphatic epoxy resins with one or more compounds possessing two groups reactive with the hydroxy group in said hydroxyaliphatic epoxy resin. The resulting product is a tetrafunctional epoxy resin wherein a pair of the hydroxyaliphatic epoxy resin molecules have been linked together through either ester or urethane linkages formed via reaction of the hydroxy group. The tetrafunctional vinyl ester resins of the present invention are prepared using the tetrafunctional epoxy resins and methods previously delineated herein for the preparation of vinyl ester resins.

Suitable compounds which are reacted with the hydroxyaliphatic epoxy resin to provide the tetrafunctional epoxy resin include most any compound possessing two groups reactive with the hydroxy group in said hydroxyaliphatic epoxy resin. Representative of said compounds are the dicarboxylic acid halides, such as, for example, oxalyl chloride, oxalyl bromide, adipoyl chloride, suberoyl chloride, sebacoyl chloride, dodecanedioyl dichloride, cyclohexanediacetic acid chloride, trans-1,4-cyclohexanedicarboxylic acid chloride, dicyclopentadienedicarboxylic acid chloride, terephthaloyl chloride, isophthaloyl dichloride, 1,4-phenylenediacetic acid chloride, 1,2-phenylenediacetic acid chloride, mixtures thereof and the like. These dicarboxylic acid halides provide the tetraepoxy resin compositions of Formula III. Additional representatives of said compounds are the diisocyanates, such as, for example, 1,6-diisocyanatohexane, 1,12-diisocyanatododecane, 1,4-diisocyanatocyclohexane, dicyclopentadiene diisocyanate, toluene diisocyanate, diphenylmethane diisocyanate, biphenyl diisocyanate, mixtures thereof and the like. These diisocyanates provide the tetraepoxy resin compounds of Formula IV. In the reaction to produce the tetraepoxy resin compositions of the present invention, both the dicarboxylic acid halides and the diisocyanates are employed in essentially stoichiometric amounts, with respect to the hydroxyl group contained in the hydroxyaliphatic epoxy resin (1:1 isocyanate group:hydroxy group or acid halide group). The coupling reaction is usually conducted at temperatures of from about −20° C. to about 80° C., preferably from about 0° C. to about 50° C., more preferably from about 10° C. to about 30° C. A suitable basic acting substance is employed to facilitate reaction of a dicarboxylic acid halide with the hydroxy group of the hydroxyaliphatic epoxy resin. Said basic acting substance additionally serves to scavenge hydrogen halide generated during the vinylization reaction, thus preventing undesirable reaction with epoxide groups. Suitable basic acting substances include the alkali metal or alkaline earth metal hydroxides, carbonates and bicarbonates and the trialkyl monoamines. Particularly suitable such compounds include sodium carbonate, potassium carbonate, sodium bicarbonate, potassium bicarbonate, magnesium carbonate, calcium carbonate, triethylamine, tri-n-butylamine, tri-tert-butylamine, mixtures thereof and the like. Care should be taken to utilize only those basic acting substances which are inert to reaction with any of the reactants employed in the vinylization reaction or the product formed therefrom. The coupling reaction is advantageously conducted in the presence of one or more solvents. Suitable such solvents include aliphatic and aromatic hydrocarbons, halogenated aliphatic hydrocarbons, aliphatic ethers, cyclic ethers, ketones, esters, amides, sulfoxides, combinations thereof and the like. Particularly suitable solvents include pentane, hexane, octane, toluene, methyl ethyl ketone, methylisobutyl ketone, dimethylformamide, dimethylsulfoxide, diethyl ether, methyl acetate, ethyl acetate, tetrahydrofuran, 1,4-dioxane, methylene chloride, chloroform, ethylene dichloride, methyl chloroform, ethylene glycol dimethyl ether, combinations thereof and the like. The solvent may be removed at the completion of the reaction using conventional means, such as, for example, vacuum distillation. Care should be taken to utilize only those solvents which are inert to reaction with any of the reactants employed in the coupling reaction or the product formed therefrom.

Polymer Modified Epoxy and Vinyl Ester Resins Derived from Hydroxyaliphatic Epoxy Resins The polymer modified epoxy resins of the present invention are prepared via copolymerization of (A) one or more partially or totally vinylized epoxy resins derived from the vinylization reaction of one or more monohydroxyaliphatic epoxy resins and (B) one or more polymerizable ethylenically unsaturated monomers. The copolymerization is effected in the usual fashion, that is, by application of heat and/or pressure, typically in the presence of one or more free radical-forming catalysts. One or more inert solvents may optionally be used in the copolymerization reaction. (The term "inert" means that little, if any, reaction between the solvent and reactants or copolymer product occurs.). Suitable polymerizable ethylenically unsaturated monomers include those previously delineated herein for the preparation of vinyl ester resins. When two or more polymerizable ethylenically unsaturated monomers are used in the copolymerization with the vinylized epoxy resin, they can be preblended and then copolymerized with the vinylized epoxy resin. Alternately, they can be added in separate additions such that blocks from each respective monomer are predominately produced. The additions are made in aliquots or continuously. These monomers or monomer mixtures are employed in an amount which provides from about 0.1 to about 150, preferably from about 1 to about 80, more preferably from about 2 to about 40 percent by weight based on the combined weight of such monomers and the vinylized epoxy resin. Suitable free radical-forming catalysts are the well known organic peroxides and hydroperoxides, and include, for example, benzoyl peroxide, di-tert-butylperoxide, tert-butylperoxybenzoate, tert-butylhydroperoxide; the azo and diazo compounds, such as, for example, azobis(isobutyronitrile); and mixtures of said free radical-forming catalysts. Said catalysts are typically used in amounts of from about 0.01 to about 5 percent by weight of the total reactants used. Reaction temperatures of from about 20° C. to about 200° C. are used for the copolymerization reaction, with temperatures of from about 30° C. to about 120° C. being preferred. Reaction times of from about 15 minutes to about 8 hours are used for the copolymerization, with times of from about 30 minutes to about 4 hours being preferred. The solvent used, if any, may be removed before further use of the copolymerization product, using conventional methods such as, for example, vacuum distillation. The copolymerization reaction may be carried out in the presence of from about 0.01 to about 2 percent by weight of one or more chain transfer agents, although this is not generally preferred. Representative chain transfer agents include the alkyl mercaptans such as butyl mercaptan and stearyl mercaptan; the disulfides and halogenated compounds, especially those containing bromine.

The product resulting from the copolymerization is a polymer modified epoxy resin, a portion or all of which contains chemically bonded (grafted) polymeric chains derived from the copolymerization of one or more polymerizable ethylenically monomers with the vinyl groups present in the vinylized epoxy resin. Said product can also contain homooligomer (cooligomer) and/or homopolymer (copolymer) of the ethylenically unsaturated monomers. Likewise, said product can also contain homooligomer (cooligomer) and/or homopolymer (copolymer) of the vinylized epoxy resin. Methodology for radical and ionic chain polymerizations are delineated by G. G. Odian in *Principles of Polymerization* published by John Wiley and Sons, New York (1981) on pages 179–507 which are incorporated herein by reference. The polymer modified vinyl ester resins of the present invention are prepared using the polymer modified epoxy resins and methods previously delineated herein for the preparation of vinyl ester resins.

Conventional Epoxy Resins and Vinyl Ester Resins

One or more epoxy resins may be mixed with the hydroxyaliphatic functional epoxy resins, the totally or partially vinylized hydroxyaliphatic epoxy resins, the tetrafunctional epoxy resins or the polymer modified epoxy resins to prepare curable mixtures of the present invention. The epoxy resins which can be employed to prepare the curable compositions of the present invention include essentially any epoxy-containing compound which contains an average of more than one vicinal epoxide group per molecule. The epoxide groups can be attached to any oxygen, sulfur or nitrogen atom or the single bonded oxygen atom attached to the carbon atom of a —CO—O— group in which said oxygen, sulfur or nitrogen atom or the carbon atom of the —CO—O— group is attached to an aliphatic, cycloaliphatic, polycycloaliphatic or aromatic hydrocarbon group which hydrocarbon group can be substituted with any inert substituent including, but not limited to, halogen atoms, preferably fluorine, bromine or chlorine, nitro groups, and the like or such groups can be attached to the terminal carbon atoms of a compound containing an average of more than one —(O—CHR$^a$—CHR$^a$)t— group where each R$^a$ is independently hydrogen or an alkyl or haloalkyl group, containing from one to about 2 carbon atoms, with the proviso that only one R$^a$ group can be a haloalkyl group, and t has a value from one to about 100, preferably from one to about 20, more preferably from one to about 10, most preferably from one to about 5.

Said epoxy resins include, for example, the diglycidyl ethers of: resorcinol, hydroquinone, 4,4'-isopropylidenediphenol (bisphenol A), 4,4'-dihydroxydiphenylmethane, 4,4'-dihydroxybenzophenone, 3,3'5,5'-tetrabromo-4,4'-isopropylidenediphenol, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachloro-4,4'-isopropylidenediphenol A, 3,3'-dimethoxy-4,4'-isopropylidenediphenol, 4,4'-dihydroxy-α-methylstilbene, 4,4'-dihydroxybenzanilide, 4,4'-dihydroxyazoxybenzene, 4,4'-dihydroxybiphenyl, 4,4'-dihydroxydiphenylazomethine, 4,4'-dihydroxydiphenylacetylene, 4,4'-dihydroxystilbene, 4,4'-dihydroxy-α-cyanostilbene, 4,4'-dihydroxyazobenzene, 4,4'-dihydroxyazoxybenzene, 4,4'-dihydroxychalcone, 4-hydroxyphenyl-4-hydroxybenzoate, dipropylene glycol, poly(propylene glycol), thiodiglycol; the triglycidyl ether of tris(hydroxyphenyl)methane; the polyglycidyl ethers of a phenol or alkyl or halogen substituted phenol-aldehyde acid catalyzed condensation product (novolac resins); the tetraglycidyl amines of: 4,4'-diaminodiphenylmethane, 4,4'-diaminostilbene, N,N'-dimethyl-4,4'-diaminostilbene, 4,4'-diaminobenzanilide, 4,4'-diaminobiphenyl, 4,4'-diamino-α-methylstilbene; the polyglycidyl ether of the condensation product of a dicyclopentadiene or an oligomer thereof and a phenol or alkyl or halogen substituted phenol; the advancement reaction products of the aforesaid di and polyglycidyl ethers with aromatic di and polyhydroxyl or carboxylic acid containing compounds including, for example hydroquinone, resorcinol, catechol, 2,4-dimethylresorcinol, 4-chlororesorcinol, tetramethylhydroquinone, 4,4'-isopropylidenediphenol (bisphenol A), 4,4'-dihydroxydiphenylmethane, 4,4'-thiodiphenol, 4,4'-sulfonyldiphenol, 2,2'-sulfonyldiphenol, 4,4'-dihydroxydiphenyl oxide, 4,4'-dihydroxybenzophenone, 1,1-bis(4-hydroxyphenyl)-1-phenylethane, 4,4'-bis(4(4-hydroxyphenoxy)-phenylsulfone)diphenyl ether, 4,4'-dihydroxydiphenyl disulfide, 3,3',3,5'-tetrachloro-4,4'-isopropylidenediphenol, 3,3',3,5'-tetrabromo-4,4'-isopropylidenediphenol, 3,3'-dimethoxy-4,4'-isopropylidenediphenol, 4,4'-dihydroxybiphenyl, 4,4'-dihydroxy-α-methylstilbene, 4,4'-dihydroxybenzanilide, bis(4-hydroxyphenyl)terephthalate, N,N'-bis(4-hydroxyphenyl)terephthalamide, bis(4'-hydroxybiphenyl) terephthalate, 4,4'-dihydroxyphenylbenzoate, bis(4'-hydroxyphenyl)-1,4-benzenediimine; 1,1'-bis(4-hydroxyphenyl)cyclohexane, phloroglucinol, pyrogallol, 2,2',5,5'-tetrahydroxydiphenyl sulfone, tris(hydroxyphenyl) methane, dicyclopentadiene diphenol, tricyclopentadiene diphenol, terephthalic acid, isophthalic acid, 4,4'-benzanilidedicarboxylic acid, 4,4'-phenylbenzoatedicarboxylic acid, 4,4'-stilbenedicarboxylic acid, adipic acid; and any combination of the aforementioned epoxy resins and the like.

One or more vinyl ester resins may be mixed with the hydroxyaliphatic functional vinyl ester resins, the totally or partially vinylized hydroxyaliphatic vinyl ester resins, the tetrafunctional vinyl ester resins or the polymer modified vinyl ester resins to prepare curable mixtures of the present invention. Said vinyl ester resins are prepared using the aforementioned epoxy resins and the methods previously delineated herein for the preparation of hydroxyaliphatic vinyl ester resins.

Other Components

The curable blends containing one or more hydroxyaliphatic functional epoxy or vinyl ester resins, totally or partially vinylized hydroxyaliphatic epoxy or vinyl ester resins, the tetrafunctional epoxy or vinyl ester resins or the polymer modified epoxy or vinyl ester resins, can be blended with other materials such as solvents or diluents, fillers, pigments, dyes, flow modifiers, thickeners, reinforcing agents, mold release agents, wetting agents, stabilizers, fire retardant agents, surfactants or any combination thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended compositions.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, xylene, methyl ethyl ketone, methyl isobutyl ketone, diethylene glycol methyl ether, dipropylene glycol methyl ether, dimethylformamide, N-methylpyrrolidinone, tetrahydrofuran, 1,4-dioxane, propylene glycol methyl ether or any combination thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include glass, ceramics, nylon, rayon, cotton, aramid, graphite, polyalkylene terephthalates, polyethylene, polypropylene, polyesters or any combination thereof and the like.

Suitable fillers which can be employed herein include, for example, inorganic oxides, ceramic microspheres, plastic microspheres, glass microspheres, inorganic whiskers, calcium carbonate or any combination thereof and the like.

The fillers can be employed in amounts suitably from about zero to about 95, more suitably from about 10 to about 80, most suitably from about 40 to about 60 percent by weight based upon the weight of the total composition.

The curable blends of the present invention can be employed in coating, casting, encapsulation, electronic or structural laminate or composite, filament winding, molding, and the like applications.

The following examples are illustrative of the present invention, but are not to be construed as to limiting its scope in any manner.

EXAMPLE 1

Copolymerization of Diglycidyl Ether of 1,2-bis(4-Hydroxyphenyl)-2-hydroxypropane and Sulfanilamide A portion (26.9 milligrams, 0.000139 epoxide equivalent) of distilled diglycidyl ether of 1,2-bis(4-hydroxyphenyl)-2-hydroxypropane having an epoxide, equivalent weight (EEW) of 193.56 and sulfanilamide (6.0 milligrams, 0.000139 N—H equivalent) were combined in an aluminum pan used for differential scanning calorimetry analysis. A second sample was prepared by combining a portion (29.2 milligrams, 0.000151 epoxide equivalent) of the distilled diglycidyl ether of 1,2-bis(4-hydroxyphenyl)-2-hydroxypropane and sulfanilamide (6.5 milligrams, 0.000151 N—H equivalent) in an aluminum pan used for differential scanning calorimetry analysis. Differential scanning calorimetry was completed by heating at a rate of 10° C. per minute under a stream of nitrogen flowing 35 cubic centimeters per minute from 30° C. to 300° C. with the average values of the two samples reported. This analysis revealed a cure exotherm with an onset of 131.3° C. and a maximum at 172.0° C. immediately followed by a second cure exotherm with an onset of 223.2° C. and a maximum of 242.0° C. The collective enthalpy for the pair of merged exotherms was 189.5 joules per gram. A second differential scanning calorimetry analysis was completed using the aforementioned conditions and revealed a glass transition temperature of 174.1° C. The rigid, transparent, light amber colored product recovered from the differential scanning calorimetry was featureless (non-birefringent) when observed by optical microscopy under crosspolarized light.

COMPARATIVE EXAMPLE 1

Copolymerization of Diglycidyl Ether of Bisphenol A (4,4'-Isopropylidenediphenol) and Sulfanilamide A portion (24.09 milligrams, 0.0001414 epoxide equivalent) of a crystalline diglycidyl ether of bisphenol A having an epoxide equivalent weight (EEW) of 170.4 and sulfanilamide (6.09 milligrams, 0.0001414 N—H equivalent) were combined in an agate mortar and ground to a homogeneous powder. Portions (17.5 and 26.4 milligrams) of the curable blend were analyzed by differential scanning calorimetry by heating at a rate of 10° C. per minute under a stream of nitrogen flowing 35 cubic centimeters per minute from 30° C. to 300° C. with the average values of the two samples reported. This analysis revealed a sharp melting point endotherm with a minimum at 56.3° C. and an enthalpy of 58.8 joules per gram. This analysis additionally revealed a broad cure exotherm with an onset of 154.0° C. and a maximum at 172.0° C. immediately followed by a second cure exotherm with an onset which could not be measured due to overlap with the initial cure exotherm and a maximum of 242.2° C. The collective enthalpy for the pair of merged exotherms was of 184.8 joules per gram. A second differential scanning calorimetry analysis was completed using the aforementioned conditions and revealed a glass transition temperature of 181.6° C. The rigid, transparent, light amber colored product recovered from the differential scanning calorimetry was featureless (non-birefringent) when observed by optical microscopy under crosspolarized light.

EXAMPLE 2

A. Isolation of 1,2-bis(4-Hydroxyphenyl)-2-hydroxypropane

A wet cake containing 1,2-bis(4-hydroxyphenyl)-2-hydroxypropane was recovered from the reaction of 1,2-bis(4-hydroxyphenyl)-2-chloropropane and calcium carbonate in aqueous media. High pressure liquid chromatographic (HPLC) analysis demonstrated the presence of 97.7 area % 1,2-bis(4-hydroxyphenyl)-2-hydroxypropane, 1.78 area % 4,4'-dihydroxy-alpha-methylstilbene and 0.51 area % of an unknown compound. A portion of the wet cake was placed in an aluminum dish, then dried 20 hours at 25° C.–27° C. in a vacuum oven to give a constant weight. The HPLC analysis of the recovered dry product was essentially unchanged (97.7 area % 1,2-bis(4-hydroxyphenyl)-2-hydroxypropane, 1.92 area % 4,4'-dihydroxy-alpha-methylstilbene and 0.40 area % of an unknown compound).

B. Uncatalyzed Copolymerization of Diglycidyl Ether of 1,2-bis(4-Hydroxyphenyl)-2-hydroxpropane and 1,2-bis(4-Hydroxyphenyl)-2-hydroxypropane: in situ Phenoxy Resin Synthesis A portion (17.3 milligrams, 0.000089 epoxide equivalent) of distilled diglycidyl ether of 1,2-bis(4-hydroxyphenyl)-2-hydroxypropane having an epoxide equivalent weight (EEW) of 193.56 and 1,2-bis(4-hydroxyphenyl)-2-hydroxypropane (10.92 milligrams, 0.000089 phenolic hydroxyl equivalent) were combined in an aluminum pan used for differential scanning calorimetry analysis. A second sample was prepared by combining a portion (18.7 milligrams, 0.000097 epoxide equivalent) of the distilled diglycidyl ether of 1,2-bis(4-hydroxyphenyl)-2-hydroxypropane and 1,2-bis(4-hydroxyphenyl)-2-hydroxypropane (11.8 milligrams, 0.000097 phenolic hydroxyl equivalent) in an aluminum pan used for differential scanning calorimetry analysis. Differential scanning calorimetry was completed by heating at a rate of 10° C. per minute under a stream of nitrogen flowing 35 cubic centimeters per minute from 30° C. to 300° C. with the average values of the two samples reported. This analysis revealed a cure exotherm with an onset of 115.7° C. and a maximum at 210.0° C. The enthalpy for the exotherm was 213.8 joules per gram. A second differential scanning calorimetry analysis was completed using the aforementioned conditions and revealed a glass transition temperature of 89.8° C. There was no residual exothermic cure noted in this second scan. The results are also summarized in Table 1.

COMPARATIVE EXAMPLE 2

Uncatalyzed Copolymerization of Diglycidyl Ether of Bisphenol A andBisphenol A: in situ Phenoxy Resin Synthesis A portion (14.48 milligrams, 0.000085 epoxide equivalent) of a crystalline diglycidyl ether of bisphenol A having an epoxide equivalent weight (EEW) of 170.4 and bisphenol A (9.70 milligrams, 0.000085 phenolic hydroxyl equivalent) were combined in an agate mortar and ground to a homogeneous powder. The bisphenol A used was a commercial grade product containing in excess of 99% 4,4'-isopropylidenediphenol. Portions (16.9 and 17.1 milligrams) of the curable blend were analyzed by differential scanning calorimetry by heating at a rate of 10° C. per minute under a stream of nitrogen flowing 35 cubic centimeters per minute from 30° C. to 300° C. with the average values of the two samples reported. This analysis revealed a sharp melting point endotherm with a minimum at 52.3° C. and an enthalpy of 43.0 joules per gram. A very broad cure exotherm with an onset of 154.0° C. and a maximum in excess of the 300° C. upper temperature limit for the analysis was additionally observed. The enthalpy for the exotherm could not be measured due to the incomplete cure under the conditions of the analysis. A second differential scanning calorimetry analysis was completed using the aforementioned conditions and revealed the presence of residual exothermic cure. The results are also summarized in Table 1.

TABLE 1

| Property | Example 2 | Comparative Example 2 |
|---|---|---|
| Initial Scan: | | |
| Minimum of melting point endotherm (° C.) | none | 52.3 |
| Enthalpy (joules/gram) | none | 43.0 |
| Onset to exothermic cure (° C.) | 115.7 | 226.0 |
| Maximum of cure exotherm (° C.) | 210.0 | >300 |
| Enthalpy (joules/gram) | 213.8 | unknown |
| Second Scan: | | |
| Glass Transition Temperature (° C.) | 89.8 | none |
| Residual cure energy | none | present |

EXAMPLE 3

Catalyzed Copolymerization of Diglycidyl Ether of 1.2-bis(4-Hydroxyphenyl)-2-hydroxypropane and 1,2-bis(4-Hydroxyphenyl)-2-hydroxypropane: in situ Phenoxy Resin Synthesis Distilled diglycidyl ether of 1,2-bis(4-hydroxyphenyl)-2-hydroxypropane (1.9356 gram, 0.01 epoxide equivalent) having an epoxide equivalent weight (EEW) of 193.56 and tetrabutylphosphonium acetate·acetic acid complex as a 70.69 weight % solids solution in methanol (0.0107 gram, 0.002 equivalent per epoxide equivalent) were thoroughly mixed together to provide a homogeneous solution. A portion (18.80 milligrams, 0.000097 epoxide equivalent) of the precatalyzed diglycidyl ether of 1,2-bis(4-hydroxyphenyl)-2-hydroxypropane and 1,2-bis(4-hydroxyphenyl)-2-hydroxypropane (11.86 milligrams, 0.000097 phenolic hydroxyl equivalent) were combined in an aluminum pan used for differential scanning calorimetry analysis. A second sample was prepared by combining a portion (21.6 milligrams, 0.000112 epoxide equivalent) of the distilled diglycidyl ether of 1,2-bis(4-hydroxyphenyl)-2-hydroxypropane and 1,2-bis(4-hydroxyphenyl)-2-hydroxypropane (13.60 milligrams, 0.000112 phenolic hydroxyl equivalent) in an aluminum pan used for differential scanning calorimetry analysis. Differential scanning calorimetry was completed by heating at a rate of 10° C. per minute under a stream of nitrogen flowing 35 cubic centimeters per minute from 30° C. to 300° C. with the average values of the two samples reported. This analysis revealed a cure exotherm with an onset of 110.5° C. and a maximum at 181.9° C. The enthalpy for the exotherm was 206.1 joules per gram. A second differential scanning calorimetry analysis was completed using the aforementioned conditions and revealed a glass transition temperature of 98.4° C. There was no residual exothermic cure noted in this second scan. The results are also summarized in Table 2.

COMPARATIVE EXAMPLE 3

Catalyzed Copolymerization of Diglycidyl Ether of Bisphenol A and Bisphenol A: in situ Phenoxy Resin Synthesis Crystalline diglycidyl ether of bisphenol A (1.7040 grams, 0.01 epoxide equivalent) having an epoxide equivalent weight (EEW) of 170.4 and tetrabutylphosphonium acetate·acetic acid complex as a 70.69 weight % solids solution in methanol (0.0107 gram, 0.002 equivalent per epoxide equivalent) were combined and then mixed with gentle heating to 50° C. to provide a homogeneous solution. Bisphenol A (1.1414 grams, 0.01 phenolic hydroxyl equivalent) was added to the warm precatalyzed diglycidyl ether with mixing until a homogeneous paste formed. The bisphenol A used was a commercial grade product containing in excess of 99% 4,4-isopropylidenediphenol. Portions (31.7 and 35.1 milligrams) of the curable blend were analyzed by differential scanning calorimetry by heating at a rate of 10° C. per minute under a stream of nitrogen flowing 35 cubic centimeters per minute from 30° C. to 300° C. with the average values of the two samples reported. This analysis revealed a cure exotherm with an onset of 119.0° C. and a maximum at 184.2° C. The enthalpy for the exotherm, was 199.2 joules per gram. A second differential scanning calorimetry analysis was completed using the aforementioned conditions and revealed a glass transition temperature of 70.4° C. There was no residual exothermic cure noted in this second scan. The results are also summarized in Table 2.

TABLE 2

| Property | Example 3 | Comparative Example 3 |
|---|---|---|
| Initial Scan: | | |
| Onset to exothermic cure (° C.) | 110.5 | 119.0 |
| Maximum of cure exotherm (° C.) | 181.9 | 184.2 |
| Enthalpy (joules/gram) | 206.1 | 199.2 |
| Second Scan: | | |
| Glass Transition Temperature (° C.) | 98.4 | 70.4 |
| Residual cure energy | none | none |

EXAMPLE 4

Copolymerization of Diglycidyl Ether of 1,2-bis(4-Hydroxyphenyl)-2-hydroxypropane With an Aliphatic/Cycloaliphatic Diamine Mixture The diglycidyl ether of 1,2-bis(4-hydroxyphenyl)-2-hydroxypropane and an aliphatic/cycloaliphatic diamine mixture were combined in 1:1 epoxide:N—H stoichiometry and mixed to give a homogeneous solution. The aliphatic/cycloaliphatic diamine mixture used was a commercial grade product containing 90 weight % diethyltoluenediamine and 10 weight % 1,2-diaminocyclohexane. Viscosity of the curable solution was monitored as a function of time at 50° C. The results are given in Table 3.

COMPARATIVE EXAMPLE 4

Copolymerization of Diglycidyl Ether of Bisphenol A (4,4'-Isopropyli-denediphenol) With an Aliphatic/Cycloaliphatic Diamine Mixture A diglycidyl ether of bisphenol A and an aliphatic/cycloaliphatic diamine mixture were combined in 1:1 epoxide:N—H stoichiometry and mixed for one minute at room temperature to give a homogeneous solution. The diglycidyl ether of bisphenol A used was a commercial grade product with an EEW specification of 176 to 183. The aliphatic/cycloaliphatic diamine mixture used was a commercial grade product containing 90 weight % diethyltoluenediamine and 10 weight % 1,2-diaminocyclohexane. Brookfield viscosity of the curable solution was monitored as a function of time at 50° C. The results are given in Table 3.

TABLE 3

| Designation | Time at 50° C. (min.) | Viscosity (cps) |
|---|---|---|
| Example 4 | 0 | 1444 |
| | 5 | 1779 |
| | 10 | 2184 |
| | 15 | 2655 |
| | 20 | 3165 |
| | 25 | 3701 |
| | 30 | 4303 |
| | 35 | 4918 |
| | 40 | 5598 |
| | 45 | 6304 |
| | 50 | 7089 |
| Comparative Example 4 | | |
| | 0 | 233 |
| | 5 | 315 |
| | 10 | 330 |
| | 15 | 349 |
| | 20 | 370 |
| | 25 | 392 |
| | 30 | 416 |
| | 35 | 441 |
| | 40 | 464 |
| | 45 | 488 |
| | 50 | 514 |
| | 120 | 908 |

EXAMPLE 5

A. Condensation Reaction of 5-Chloro-2-pentanone and Phenol

5-Chloro-2-pentanone (36.17 grams, 0.30 mole) and phenol (282.3 grams, 3.0 mole) were added to a three-neck, round-bottom, one liter, glass reactor and heated to 35° C. with magnetic stirring under a nitrogen atmosphere (0.5 liter per minute) and under a condenser chilled to −10° C. 3-Mercaptopropanesulfonic acid (9.37 grams, 0.06 mole) was added to the solution which was then maintained for the 15.8 hours at a temperature of 34° C.–37° C. The product solution was recovered from the reactor and added to stirred, deionized water (3.5 liters). The stirred slurry was then added to a separatory funnel and the organic layer allowed to settle out. The recovered organic layer was then added back into the clean separatory funnel and washed with a solution of sodium bicarbonate (30 grams) in deionized water (800 milliliters). The organic layer which settled out was recovered, added back into the clean separatory funnel, then washed with deionized water (800 milliliters). The resulting organic layer which settled out (99.1 grams) was added to a single-neck, round-bottom flask along with sodium bicarbonate (5 grams), then rotary evaporated using final conditions of 1 mm Hg vacuum at 95° C. for 3.8 hours. The recovered product was dissolved into ethyl acetate (250 milliliters) then twice washed in a separatory funnel with deionized water (150 grams per portion). The washed ethyl acetate solution was recovered and rotary evaporated to provide 46.0 grams of a transparent, amber colored, glassy product (at room temperature). HPLC analysis (unnormalized) revealed a single major product peak comprising 88 area %, 6 area % phenol and several minor peaks comprising the balance.

B. Acetoxylation of 2,2'-bis(4-Hydroxphenyl)-5-chloropentane

A portion (43.7 grams) of the 2,2'-bis(4-hydroxyphenyl)-5-chloropentane from A above, acetic acid (250 milliliters), acetic anhydride (50 milliliters) and potassium acetate (46.8 grams, 0.475 mole) were added to a three-neck, round-bottom, one liter, glass reactor and heated to reflux with magnetic stirring under a nitrogen atmosphere (0.5 liter per minute) and under a condenser chilled to −10° C. After 3.2 hours, the product slurry was sampled for HPLC analysis (unnormalized) and revealed the presence of a single major product peak for the acetoxylated product comprising 82 area % with several minor peaks comprising the balance and complete conversion of the 2,2'-bis(4-hydroxyphenyl)-5-chloropentane. At this time, the reactor was cooled to 25° C. and the product diluted with methylene chloride (150 milliliters). The product solution was recovered from the reactor then added to a separatory funnel and twice washed with deionized water (100 milliliters). The organic layer which settled out was recovered, then rotary evaporated to provide 34.9 grams of a transparent, amber colored, viscous liquid product (at room temperature). HPLC analysis (unnormalized) revealed a single major product peak comprising 90 area %, with several minor peaks comprising the balance.

C. Hydrolysis of Acetoxylated 2,2'-bis(4-Hydroxyphenyl)-5-chloropentane

A portion (34.0 grams) of the acetoxylated 2,2'-bis(4-hydroxyphenyl)-5chloropentane from B above and sodium hydroxide (21.0 grams, 0.526 mole) dissolved in deionized water (400 milliliters) were added to a three-neck, round-bottom, one liter, glass reactor and heated to reflux with magnetic stirring under a nitrogen atmosphere (0.5 liter per minute) and under a condenser chilled to 10° C. After 3 hours at the 98° C. reflux temperature, the product slurry was sampled for HPLC analysis (unnormalized, sample acidified with aqueous hydrochloric acid) and revealed the presence of a single major product peak for the hydrolyzed product comprising 87 area %, 3 area % phenol and several minor peaks comprising the balance and complete conversion of the acetoxylated 2,2-bis(4-hydroxyphenyl)-5-chloropentane. At this time, the reactor was cooled to 25° C. and the product neutralized using aqueous hydrochloric acid followed by rotary evaporation to remove water. The resultant solid product was diluted with ethyl acetate (200 milliliters) and the product slurry obtained was recovered then added to a separatory funnel and twice washed with deionized water (100 milliliters). The organic layer which settled out was recovered, then rotary evaporated to provide 19.7 grams of a transparent, amber colored, glassy product (at room temperature). HPLC analysis (unnormalized) revealed a single major product peak comprising 90 area %, 0.86 area % phenol, with several minor peaks comprising the balance.

D. Epoxidation of 2,2'-bis(4-Hydroxyphenyl)-5-hydroxypentane

A portion (0.136 phenolic hydroxyl equivalent, 18.55 grams) of the 2,2'-bis(4-hydroxyphenyl)-5-hydroxypentane from C above, epichlorohydrin (63.0 grams, 0.68 mole), ethanol (35 weight % of the epichlorohydrin used, 22.1 grams), and deionized water (8 weight % of the epichlorohydrin used) were added to a three-neck, round-bottom, one liter, glass reactor and heated to a 60° C. solution with magnetic stirring under a nitrogen atmosphere (0.5 liter per minute) and under a condenser chilled to −10° C. Once the 60° C. temperature was achieved, dropwise addition of a solution of 97+% sodium hydroxide (4.90 grams, 0.123 mole) dissolved in deionized water (24.5 milliliters) commenced and was completed over a 45 minute period with maintenance of the reaction temperature at 58° C.–60° C. Ten minutes after completion of the aqueous sodium hydroxide addition, stirring ceased and the aqueous brine layer settled out and was pipetted off and discarded. Fifteen minutes after the completion of the aqueous sodium hydroxide addition, a second solution of 97+% sodium hydroxide (2.2 grams, 0.055 mole) dissolved in deionized water (10.9 milliliters) commenced and was completed over a 20 minute period with maintenance of the reaction temperature at 57° C.–61° C. Fifteen minutes after completion of the aqueous sodium hydroxide addition, the product mixture was recovered from the reactor and added to a separatory funnel and the aqueous layer allowed to settle out. After removal of the aqueous layer, the remaining organic layer was sequentially washed four times in a separatory funnel with deionized water (100 grams per portion). The washed organic layer was recovered and rotary evaporated using final conditions of 1 mm Hg vacuum at 85° C. for 45 minutes to provide 24.6 grams of a transparent, light amber colored, tacky solid (at room temperature). HPLC analysis (unnormalized) revealed a single major product peak (with a second peak as a shoulder) comprising 92.3 area %, 0.61 area % phenyl glycidyl ether and a pair of minor peaks comprising the balance. Fourier transform infrared spectrophotometric analysis of a neat film of the epoxy resin on a potassium bromide plate confirmed the presence of the expected aliphatic hydroxyl functionality. Titration for percent epoxide versus a standard diglycidyl ether of 4,4'-isopropylidenediphenol revealed the presence of 22.13% epoxide (194.5 EEW).

EXAMPLE 6

Uncatalyzed Copolymerization of Diglycidyl Ether of 2,2'-bis(4-Hydroxyphenyl)-5-hydroxypentane and 2,2'-bis(4-Hydroxyphenyl)-5-hydroxypentane: in situ Phenoxy Resin Synthesis A portion (0.2326 gram, 0.001196 epoxide equivalent) of the diglycidyl ether of 2,2'-bis(4-hydroxyphenyl)-5-hydroxypentane from 5-D above having an EEW of 194.5 and 2,2'-bis(4-hydroxyphenyl)-5-hydroxypentane (0.1628 gram, 0.001196 phenolic hydroxyl equivalent) from 5-C above were thoroughly mixed together to provide a homogeneous paste. Portions (17.0 and 35.8 milligrams) of the homogeneous paste were used for differential scanning calorimetry analysis. Differential scanning calorimetry was completed by heating at a rate of 10° C. per minute under a stream of nitrogen flowing 35 cubic centimeters per minute from 30° C. to 300° C. with the average values of the two samples reported. This analysis revealed a cure exotherm with an onset of 134.5° C. and a maximum at 282.8° C. A second differential scanning calorimetry analysis was completed using the aforementioned conditions and revealed a glass transition temperature of 82.7° C. There was no residual exothermic cure noted in this second scan. The results are also summarized in Table 4.

TABLE 4

| Property | Example 6 | Comparative Example 2 |
| --- | --- | --- |
| Initial Scan: | | |
| Minimum of melting point endotherm (° C.) | none | 52.3 |
| Enthalpy (joules/gram) | none | 43.0 |
| Onset to exothermic cure (° C.) | 134.5 | 226.0 |
| Maximum of cure exotherm (° C.) | 282.8 | >300 |
| Enthalpy (joules/gram) | unknown | Unknown |
| Second Scan: | | |
| Glass Transition Temperature (° C.) | 82.7 | None |
| Residual cure energy | none | Present |

EXAMPLE 7

Copolymerization of Diglycidyl Ether of 2,2'-bis(4-Hydroxyphenyl)-5- hydroxypentane With an Aliphatic/Cycloaliphatic Diamine Mixture The diglycidyl ether of 2,2'-bis(4-hydroxyphenyl)-5-hydroxypentane from 5-D and an aliphatic/cycloaliphatic diamine mixture were combined in 1:1 epoxide:N—H stoichiometry and mixed to give a homogeneous solution. The aliphatic/cycloaliphatic diamine mixture used was a commercial grade procuct containing 90 weight % diethyltoluenediamine and 10 weight % 1,2-diaminocyclohexane. Viscosity of the curable solution was monitored as a function of time at 50° C. The result are given in Table 5. These results may be compared directly with those given in Comparative Example 4 (Table 3).

TABLE 4

| Designation | Time at 50° C. (min.) | Viscosity (cps) |
| --- | --- | --- |
| Example 7 | 1 | 4403 |
| | 2 | 5426 |
| | 3 | 6881 |
| | 4 | 8925 |
| | 5 | 11,750 |
| | 6 | 15,610 |
| | 7 | 20,950 |
| | 8 | 28,460 |
| | 9 | 38,960 |
| | 10 | 53,860 |
| | 11 | 74,550 |

EXAMPLE 8

Methacrylation of Diglycidyl Ether of 2,2'-bis(4-Hydroxyphenyl)-5-hydroxypentane A portion (3.89 grams, 0.01 aliphatic hydroxyl equivalent) of the diglycidyl ether of 2,2'-bis(4-hydroxyphenyl)-5-hydroxypentane from 5-D above having an EEW of 194.5, anhydrous tetrahydrofuran (150 grams) and anhydrous −325 mesh potassium carbonate (1.52 grams, 0.011 mole) were added to a three-neck, round-bottom, one liter, glass reactor and maintained at room temperature (22° C.) with magnetic stirring under a nitrogen atmosphere (0.5 liter per minute) and under a condenser chilled to −15° C. Methacryloyl chloride (1.15 grams, 0.011 mole) was added to the stirred slurry, followed five minutes later by addition of triethylamine (1.11 gram, 0.011 mole). After 16 hours, the product slurry was sampled for HPLC analysis and revealed the presence of a single major product peak for the methacrylate product accompanied by complete conversion of the diglycidyl ether of 2,2'-bis(4-hydroxyphenyl)-5-hydroxypentane.

EXAMPLE 9

Coupling of Diglycidyl Ether of 1,2-bis(4-Hydroxyphenyl)-2-hydroxypropane with 4,4'-Diisocyanatodiphenyl Methane A portion (3.56 grams, 0.01 aliphatic hydroxy equivalent) of distilled diglycidyl ether of 1,2-bis(4-hydroxyphenyl)-2-hydroxypropane having an EEW of 193.56 was added to a predried, single-neck, 250 milliliter, glass reactor containing a dried magnetic stir bar and maintained in a dry nitrogen glovebox. Anhydrous, inhibitor free tetrahydrofuran (50 grams) which had been chromatographically purified over dry alumina in the dry, nitrogen glovebox was added to the reactor and magnetic stirring initiated to form a solution. Dibutyltin dilaurate catalyst (0.097 gram, 2.0 weight percent of the reactants used) was added to the magnetically stirred solution, followed by the dropwise addition of molten, dimer free=4,4'-diisocyanatodiphenyl methane (1.31 grams, 0.0105 isocyanate equivalent). The reaction mixture was heated at 40° C. for 30 minutes, followed by HPLC analysis of a portion of the product. The HPLC analysis revealed complete conversion of the 1,2-bis(4-hydroxyphenyl)-2-hydroxypropane and the 4,4'-diisocyanatodiphenyl methane to a single product peak proposed to be the tetraglycidyl ether.

What is claimed is:

1. A resin having the structural Formula I

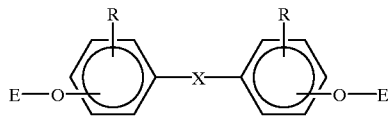

Formula I wherein each R is independently selected from the group consisting of hydrogen, a hydrocarbyl or hydrocarbyloxy group having from one to about 10 carbon atoms, a halogen atom, a nitro group, a nitrile group and a —CO—$R^2$ group; each E is independently selected from the group consisting of

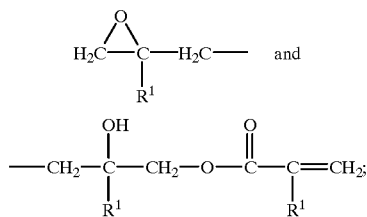

and each $R^1$ is independently selected from the group consisting of hydrogen and a hydrocarbyl group having from one to about 10 carbon atoms; X is independently selected from the group consisting of

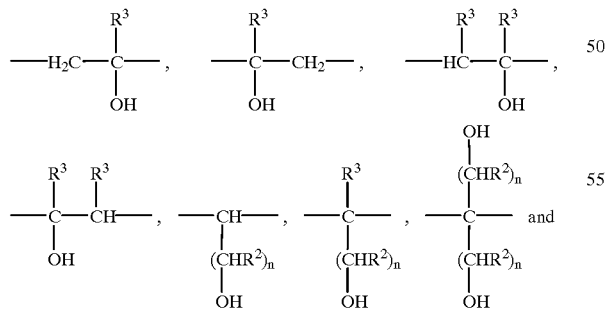

and

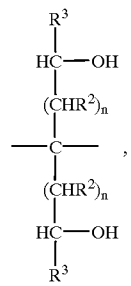

each $R^2$ is independently selected from the group consisting of hydrogen and a hydrocarbyl group having from one to about 10 carbon atoms; $R^3$ is a hydrocarbyl group having from one to about 10 carbon atoms; and n has a value of from one to about 10.

2. A resin of claim 1 wherein E is

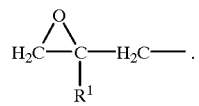

3. A resin of claim 1 wherein E is

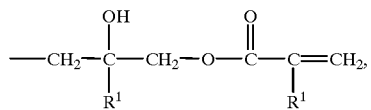

4. A resin of claim 1 wherein each R is hydrogen.
5. A resin of claim 1 wherein $R^1$ is hydrogen.
6. A resin of claim 1 wherein X is

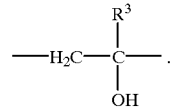

7. A resin of claim 1 wherein X is

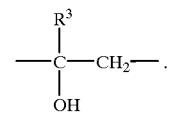

8. A resin of claim 1 wherein X is

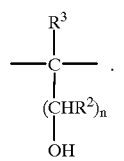

* * * * *